United States Patent [19]

Nishino et al.

[11] Patent Number: 5,093,505
[45] Date of Patent: Mar. 3, 1992

[54] HETEROCYCLIC COMPOUND, CARCINOSTATIC AGENT, AND CARCINOMA CONTROLLING METHOD

[75] Inventors: Hoyoku Nishino, Hirakata; Yukihiro Kodera, Hiroshima; Toshihiko Sumida, Hiroshima; Susumu Yoshida, Hiroshima; Hiromichi Matsuura, Hiroshima; Yoichi Itakura, Hiroshima, all of Japan

[73] Assignee: Wakunaga Seiyaku Kabushiki Kaisha, Osaka, Japan

[21] Appl. No.: 528,826

[22] Filed: May 25, 1990

[30] Foreign Application Priority Data

May 26, 1989 [JP] Japan .................. 1-134027

[51] Int. Cl.$^5$ .......................... C07D 315/00
[52] U.S. Cl. ........................ 549/417; 549/418
[58] Field of Search .............. 549/291, 292, 294, 417, 549/418; 514/460

[56] References Cited

U.S. PATENT DOCUMENTS 4,891,361  1/1990  Hatae ...................... 514/58

OTHER PUBLICATIONS

Nishino et al, J. Kyoto Pref. Univ. Med. 96(3), 279–282, 1987.

Chem. Pharm. Bull., vol. 37, No. 6, Jun. 1989, Kodera et al., pp. 1656–1658.
The Merck Index, Ninth Edition, p. 5168.
Cancer Research, vol. 43, Sep. 1983, pp. 4216–4220, Ishida et al.
Stedman's Medical Dictionary, "carcinostatic" entry.
Allixin, A Stress Compound from Garlic Chem. Absts. 112, 1990, #73738n, Yukihivo et al.

Primary Examiner—Thurman K. Page
Assistant Examiner—G. S. Kishore
Attorney, Agent, or Firm—Oblon, Spivak, McClelland, Maier & Neustadt

[57] ABSTRACT

Heterocyclic compounds of the general formula:

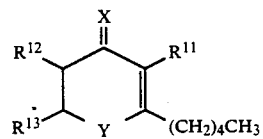

wherein $R^{11}$ is a hydroxyl group or a lower alkoxy group, $R^{12}$ is a lower alkoxy group, $R^{13}$ is a saturated or unsaturated hydrocarbon group, X is an oxygen atom or a sulfur atom, and Y is an oxygen atom or —NH— which may have a lower alkyl substituent, or salts thereof are novel and effective in controlling carcinoma.

6 Claims, 7 Drawing Sheets

HETEROCYCLIC COMPOUND, CARCINOSTATIC AGENT, AND CARCINOMA CONTROLLING METHOD

This invention relates to novel heterocyclic compounds useful as carcinostatic agents and a carcinoma controlling method.

BACKGROUND OF THE INVENTION

It is generally believed that two independent stages known as initiation and promotion participate in chemical carcinogenesis. This theory, known as the two-stage theory of carcinogenesis, was proposed by Berenblum in Cancer Res., 1, 807–814 (1941). The initiation stage is an irreversible reaction in which a chemical material known as an initiator induces a DNA change. The most widely known initiator is dimethylbenzanthracene (DMBA).

The next stage is the promotion stage in which a chemical material known as a promoter leads cells to eventual canceration. Among carcinogenesis promoters, croton oil extracted from croton seeds or its predominant ingredient, 12-O-tetradecanoylphorbol 13-acetate (TPA) is known to be highly active. At present, there have been found in the environment a number of carcinogenesis promoters having different chemical structures from TPA. Among these promoters, some act in the same mechanism as TPA (TPA type promoters) and some act in a different mechanism from TPA (non-TPA type promoters).

Recently, it was discovered that bile acids and hormones which are biological products can become promoters. It has been and will be discovered that many familiar substances can be carcinogenesis promoters as exemplified by the discovery that sodium chloride can be a gastric carcinoma promoter.

There is a need for the development of a novel carcinostatic agent capable of restraining carcinogenesis promotion an controlling carcinoma.

SUMMARY OF THE INVENTION

The inventors have succeeded in isolating compounds having a gamma-pyrone ring from garlic, and found that the compounds as such and derivatives and analogues thereof have carcinostatic action.

Broadly stated, the present invention pertains to the use of a compound of the general formula:

$$\text{(I)}$$

[structure with $R^3$, $R^2$, $R^4$, $R^1$, X, Y]

wherein $R^1$ is selected from the group consisting of a hydrogen atom, a lower alkyl group, and a styryl group which may be substituted with a hydroxyl group, a lower alkoxy group or a halogen atom at the m or p-position, $R^2$ and $R^3$ are independently selected from the group consisting of a hydrogen atom, a hydroxyl group, a lower alkoxy group, and an acyl group, $R^4$ is a hydrogen atom or a lower alkyl group, X is an oxygen atom or a sulfur atom, and Y is an oxygen atom or —NH— optionally having a lower alkyl substituent, or a salt thereof as an active ingredient of a carcinostatic agent.

The present invention provides a method for controlling carcinoma, comprising the step of administering an effective amount of a compound of formula (I).

In a narrow sense, the present invention pertains to heterocyclic compounds of the general formula:

$$\text{(II)}$$

[structure with $R^{12}$, $R^{11}$, $R^{13}$, Y, $(CH_2)_4CH_3$, X]

wherein $R^{11}$ is a hydroxyl group or a lower alkoxy group, $R^{12}$ is a lower alkoxy group, $R^{13}$ is a lower alkyl group, X is an oxygen atom or a sulfur atom, and Y is an oxygen atom or —NH— optionally having a lower alkyl substituent, or salts thereof. These heterocyclic compounds are novel.

Also contemplated is a carcinostatic agent comprising an effective amount of a heterocyclic compound of formula (II) or a salt thereof as an active ingredient.

The carcinostatic agent of the invention finds a wide range of application including cancer treatment and cancer prevention because it can restrain a carcinogenesis promotion stage and at the same time, control carcinoma. The novel heterocyclic compounds of the invention serve as an active ingredient of a carcinostatic agent, but are also expected as novel biologically active materials.

DETAILED DESCRIPTION OF THE INVENTION

Heterocyclic Compounds and Salts Thereof

Figure 1:
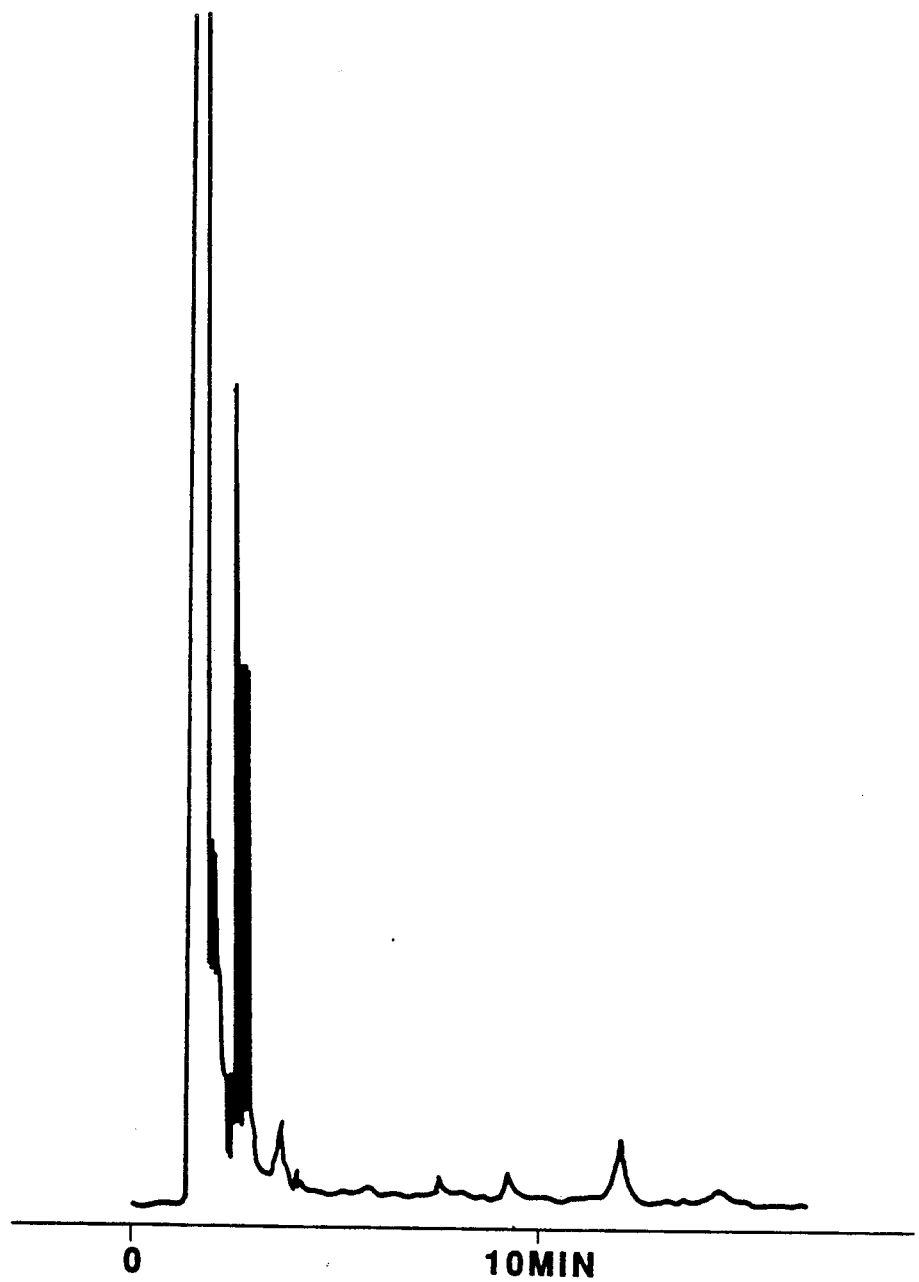
FIG. 1 is a diagram showing the elution pattern by HPLC of an extract liquid of a non-treated garlic sample.

The heterocyclic compounds of the invention are of formula (II).

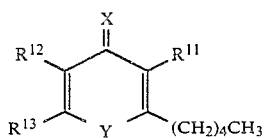

In formula (II), $R^{11}$ is a hydroxyl group or a lower alkoxy group, $R^{12}$ is a lower alkoxy group, and $R^{13}$ is a lower alkyl group. X is an oxygen atom or a sulfur atom, and Y is an oxygen atom or —NH—. The NH group represented by Y may have a lower alkyl substituent. The saturated or unsaturated hydrocarbon groups include saturated and unsaturated, linear and branched hydrocarbon groups having 1 to 6 carbon atoms, preferably saturated linear alkyl groups having 1 to 6 carbon atoms, typically methyl, ethyl, and propyl groups. The lower alkoxy groups include saturated and unsaturated, linear and branched alkoxy groups having 1 to 6 carbon atoms, preferably methoxy, ethoxy, and propoxy groups.

Several, non-limiting examples of the heterocyclic compounds of formula (II) are given below. It is to be appreciated that since compound (1) is a basic compound among a series of compounds, its physical and chemical properties are also reported.

Compound (1)
3-hydroxy-6-methyl-5-methoxy-2-pentyl-4H-pyran-4-one 1) appearance: colorless needles
2) solubility: soluble in organic solvents such as methanol, acetone, chloroform, hexane, and ethyl acetate; difficultly soluble in water
3) Mass spectrum: 226 (M+) detected in EI-MS
4) UV spectrum: γmax 279 nm, ε: 10500 in methanol
5) IR spectrum: 3250 cm$^{-1}$ (OH), 1660 cm$^{-1}$ ($\alpha,\beta$-unsaturated ketone in the pyrone ring)
6) 1H-NMR: 6.48 (—OH), 3.90 (—OCH$_3$), 2.69 (1'—H), 2.32 (C—CH$_3$), 1.66 (2'—H), 1.35 (3'—H, 4'—H), 0.90 (5'—H) in chloroform-d1
7) 13C-NMR: 150.3 (C-2), 141.9 (C-3), 169.5 (C-4), 141.9 (C-5), 158.0 (C-6), 15.0 (C-7), 26.3 (C-1'), 28.3 (C-2'), 31.2 (C-3'), 22.3 (C-4'), 13.9 (C-5'), 60.1 (—OCH$_3$)
8) melting point: 80°–81° C. (without correction)

|  | C: 63.70 | H: 8.02 |
|---|---|---|
| Theory | C: 63.38 | H: 8.17 |
| Found |  |  |

10) Molecular weight
Theory 226.27182
Compound (2)
6-methyl-3,5-dimethoxy-2-pentyl-4H-pyran-4-one
Compound (3)
3-hydroxy-6-methyl-5-methoxy-2-pentyl-4H-pyran-4-thione
Compound (4)
3-hydroxy-6-methyl-5-methoxy 2-pentyl-4-pyridone
Compound (5)
3-hydroxy-1,6-dimethyl-5-methoxy 2-pentyl-4-pyridone
Compound (6)
3-hydroxy-6-methyl-5-methoxy-2-pentyl-4-pyridinethione
Compound (7)
3-hydroxy-1,6-dimethyl-5-methoxy-2-pentyl 4-pyridinethione The foregoing compounds may form acid or base addition salts with any acids or bases and such salts are included within the scope of the invention.

Examples of the acid addition salt include salts with mineral acids such as hydrochloric acid and sulfuric acid; salts with organic carboxylic acids such as formic acid, citric acid, and trichloroacetic acid; and salts with sulfonic acids such as methanesulfonic acid, benzenesulfonic acid, p-toluenesulfonic acid, and mesitylenesulfonic acid. Examples of the base addition salt include salts with alkali metals such as sodium and potassium; salts with alkaline earth metals such as calcium and magnesium; ammonium salts; and salts with nitrogenous organic bases such as trimethylamine, triethylamine, N,N-dimethylaniline, pyridine, diethylamine, and dichlorohexylamine.

Carcinostatic Agents

One form of the present invention provides a carcinostatic agent comprising a heterocyclic compound of formula (II) or a salt thereof as an active ingredient.

Broadly stated, the present invention provides a carcinostatic agent comprising a compound of formula (I) or a salt thereof as an active ingredient.

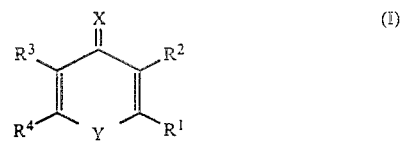

In formula (I), $R^1$ is selected from the group consisting of a hydrogen atom, a saturated or unsaturated hydrocarbon group, and a styryl group which may be substituted with a hydroxyl group, a lower alkoxy group or a halogen atom at the m or p-position, $R^2$ and $R^3$ are independently selected from the group consisting of a hydrogen atom, a hydroxyl group, a lower alkoxy group, and an acyl group, $R^4$ is a hydrogen atom or a saturated or unsaturated hydrocarbon group, X is an oxygen atom or a sulfur atom, and Y is an oxygen atom or —NH— optionally having a lower alkyl substituent.

The saturated or unsaturated hydrocarbon groups include saturated and unsaturated, linear and branched hydrocarbon groups having 1 to 6 carbon atoms, for example, hexyl, pentyl, butyl, isobutyl, tert-butyl, 1-hexenyl, 4-pentenyl, 1,3-hexadienyl, 1,3-butadienyl, 2-penten-4-ynyl, 4-pentynyl, cyclohexyl groups, preferably saturated linear alkyl groups having 1 to 6 carbon atoms, typically methyl, ethyl, and propyl groups. The lower alkoxy groups include saturated and unsaturated, linear and branched alkoxy groups having 1 to 6 carbon atoms, with methoxy, ethoxy, and propoxy groups being preferred. The acyl groups include acyl groups having 2 to 7 carbon atoms, preferably acyl groups having 2 to 3 carbon atoms. The halogen atoms include bromo, chloro, and fluoro, with chloro being preferred.

Several, non-limiting examples of the compound of formula (I) include the following compounds in addition to the novel heterocyclic compounds previously identified as compounds (1) to (7).

Compound (8)
maltol or 3-hydroxy-2-methyl 4H-pyran-4-one
Compound (9)
3-hydroxy-2-methyl-4H-pyran-4-thione Compound (10)
3-hydroxy-6-styryl-4H-pyran-4-one
Compound (11)
3-hydroxy-6-(p-methoxystyryl)-4H-pyran-4-one
Compound (12)
3-hydroxy-6-(p-chlorostyryl)-4H-pyran-4-one
Compound (13)
kojic acid or 5-hydroxy-2-hydroxymethyl-4H-pyran-4-one These compounds (8) to (13) are described in Bulletin of the Chemical Society of Japan, 50 (8), 2161 (1977) and commercially available. Among them, compound (8) or maltol is used as a food additive for stabilization and anti-oxidation purposes, and compound (13) or kojic acid is used as a skin beautifier in the cosmetic field.

As do the novel heterocyclic compounds, these compounds may form acid or base addition salts with any acids or bases and such salts are included within the scope of the invention.

The carcinostatic agent may be formed of a compound of formula (I) or a salt thereof alone or in admixture with any desired pharmaceutically acceptable additives, for example, vehicles (e.g., glucose, starch, and lactose), disintegrators (e.g., CMC-Ca), binders (e.g., hydroxypropyl cellulose, tragacanth, gelatin, and CMC-Na), flavors, lubricants, coating agents, emulsifiers, suspending agents, preservatives, stabilizers, pH adjusting agents, bases, solubilizers, isotonic agents, suppository bases, antiseptic agents, bactricides, coloring agents, perfumes, viscosity adjusting agents, plasticizers, humectants, indolent agents, and buffers. The agent may take any desired shape including powders (including fine powders), granules (including coated granules), dry syrups, hard capsules, soft capsules, tablets (plain tablets, coated tablets, three-layer tablets, core-shell tablets, sugar-coated tablets, chewing tablets, vesicants, and sublingual tablets), ointments, ophthalmic ointments, plasters, lotions, suspensions, syrups, emulsions, poultices, suppositories, injections, eye drops, and aerosols. The agent may be administered orally or non-orally.

The dose of the carcinostatic agent varies with the age, weight, and state of the patient. The daily dose is usually in the range of about 10 mg to about 10 grams, preferably about 50 mg to about 5 grams of the present compound for adults when orally administered. The preferred form of the carcinostatic agent is provided as a unit dose form for administering the daily dose in a single dosage or divided dosage form. If desired, any desired other active agents may be blended with the present compound.

The present compounds are generally considered low toxic as demonstrated by the toxicity of compound (1) having an LD50 value of at least 1,000 mg/kg when orally administered to rats and mice.

Carcinostatic Action

The carcinostatic agent of the invention has both a carcinogenesis suppression or anti-carcinogenesis-promoter effect and a carcinostatic effect. The action of the carcinostatic agent covers an overall cancer therapy field including cancer treatment and prevention.

Therefor, the carcinostatic agent of the invention is useful for the treatment of lung, skin, stomach, bladder, colon, breast, liver, prostate, intestine, rectum, pancreas, uterine, gullet, thyroid, pharynx, kidney, spleen, tongue, brain, pituitary, and nasal cancers.

Preparation Method

1. Obtainment of compound (1)

Compound (1) is a so-called stress compound which is produced by an Allium genus plant when it is damaged. By the term damage is meant that a physical, chemical or biological action is applied to a plant to such an extent as not to kill its whole cells. More particularly, the damage includes an injury by a knife, partial cell necrosis by a chemical material such as mercuric chloride and hydrogen peroxide, enzymatic lesion in cells, and infection by microorganisms such as bacteria and virus. (See I. Uritani, Kagaku to Seibutsu, 12, 546 (1974), Perrin and Bottomley, J. Am. Chem. Soc., 84, 19191 (1962), and Tomiyama et al., Phytopathology, 58, 115 (1968), for example.)

Compound (1) can be obtained from such an Allium genus plant having undergone a certain damage after one day to several months, preferably after about 10 to 20 days from the day of damage, through extraction and isolation.

The Allium genus plant includes plants belonging to the Liliaceae and Allium genuses. Most often, it is *Allium sativum L.* commonly known as garlic.

A portion of the plant from which the end substance can be obtained may be a whole plant, but preferably a bulb portion which contains small bulbar segments grown in divided sphere form. The Allium genus plant used to obtain compound (1) may also be a cell mass obtained by tissue culture, callus, or reproduced plant.

Compound (1) according to the present invention may be prepared by subjecting an Allium genus plant having a stress applied thereto as previously described to the following steps (a) to (d).

(a) Extraction

Extraction may be carried out by any desired methods commonly used in the field of crude drugs. Extraction may be carried out by immersing the plant in a hydrous or anhydrous organic solvent which is miscible with water in any desired proportion, or a water-immiscible organic solvent. The organic solvent used as the extracting solvent include water-miscible solvents such as lower alcohols (typically monohydric alcohols having 1 to 3 carbon atoms), acetone, and acetonitrile, and water-immiscible solvents such as chloroform, ethyl acetate, and hexane. The preferred solvents are monohydric alcohols having 1 to 3 carbon atoms, with methanol being most preferred.

Extraction may be done at elevated temperatures or room temperature and under atmospheric pressure or increased pressures. The plant is preferably masticated before extraction for increased efficiency.

It is also possible to carry out supercritical gas extraction using carbon dioxide or a similar gas.

(b) Fractionation

The extract fluid is stripped of the extracting solvent, suspended in water, and then extracted with an organic solvent capable of partition with water. The solvents partitionable with water include chloroform, ethyl acetate, and benzene, with chloroform being preferred.

(c) Purification by normal and reverse phase column chromatography

The fraction is stripped of the solvent and then isolated by normal and/or reverse phase column chromatography, obtaining the end substance, compound (1).

The normal phase column chromatography is a column chromatography using as a solid phase carrier a highly polar resin such as silicic acid and silica gel and as a mobile phase a solvent which is less polar than the solid phase carrier, for example, a nonpolar solvent such as chloroform, dichloromethane, hexane and ethyl acetate or a mixture thereof. For example, purification may be carried out by means of a silica gel chromatograph using a hexane-ethyl acetate (1:1) mixture as a developing solvent as will be described in Example.

The reverse phase column chromatography is a column chromatography using as a solid phase carrier a less polar resin, for example, silica gel having chemically bonded thereto a silane having a hydrocarbon residue with 1 to 18 carbon atoms, such as dimethylsilane, octadecylsilane, and octylsilane, a styrene-divinyl benzene copolymer, or a gel filtration agent. The mobile phase used herein may be any desired solvent which is more polar than the solid phase carrier. For example, a mixture of a hydrous or anhydrous water-miscible organic solvent such as a lower alcohol, acetone and acetonitrile and water may be used. Preferred are hydrous or anhydrous lower alcohols, especially monohydric alcohols having 1 to 3 carbon atoms. For example, purification may be carried out by means of a reverse phase chromatograph using a MCI-GEL ® CHP20P carrier (styrene-divinyl benzene copolymer, Mitsubishi Chemicals K.K.) and a methanol-water (9:1) mixture as a developing solvent as will be described in Example.

(d) Purification by recrystallization

The fraction resulting from (c) is stripped of the solvent and then isolated by recrystallization from a mixture of a water-miscible organic solvent and water. The water-miscible organic solvent used herein is selected from lower alcohols as previously defined (typically monohydric alcohols having 1 to 3 carbon atoms), acetone, and acetonitrile, with methanol being preferred. For example, purification may be carried out by recrystallization from a methanol-water mixture as will be described in Example.

2. Synthesis of compounds other than compound (1)

Compounds other than compound (1) may be derived from compound (1) by any desired method suitable for a particular derivation purpose. Such derivation may be carried out through alkylation, acylation, reduction, oxidation, hydrolysis, or conversion from an oxygen atom to a nitrogen or sulfur atom by a well-known method (see Inamoto trans., "Synthesis of Organic Compounds in Terms of Functional Groups," Volumes I and II, Hirokawa Publishing K.K.).

The 4H-pyran-4-thione derivatives can be synthesized by reaction of corresponding 4H-pyran-4-one with phosphorus pentasulfide in a hydroxyl group-free solvent, preferably benzene or toluene. The reaction may be effected at elevated temperatures or room temperature, with heating near the boiling point of the solvent being most preferred.

The 4-pyridone and 4-pyridinethione derivatives can be synthesized by reaction of corresponding 4H-pyran-4-one and 4H-pyran-4-thione with ammonia or a lower alkyl amine. The reaction may be effected at elevated temperatures or room temperature. The lower alkyl amines used herein have 1 to 6 carbon atoms, preferably 1 to 3 carbon atoms.

The alkylation and acylation may be carried out by any desired method commonly used in the field of chemical synthesis.

EXAMPLE

Examples of the present invention are given below by way of illustration and not by way of limitation.

EXAMPLE 1

Obtainment of Compound (1)

About 11 kg of damaged garlic was ground with an approximately triple volume of methanol. The ground garlic was squeezed using gauze. The juice was concentrated in vacuum. The concentrate was suspended in about 5 liters of water, extracted three times with about 5 liters of chloroform. The chloroform extracted fraction was concentrated in vacuum and fractionated by means of a silica gel column chromatograph. The column had a diameter of 7 cm and a length of 60 cm, the silica gel was Silica Gel 60 with a size of 230-400 mesh (by Merck), and the developing solvent used was a hexane-ethyl acetate (1:1) mixture.

The fraction containing compound (1) was concentrated in vacuum, and the compound was isolated by means of a reverse phase column chromatograph. The column had a diameter of 6 cm and a length of 40 cm, the resin was MCI-GEL ® CHP20P (by Mitsubishi Chemicals K.K.), and the developing solvent used was a methanol-water (9:1) mixture.

The product was recrystallized from a water-methanol mixture, filtered, and then dried in vacuum.

There was obtained about 14 grams of crystals or compounds (1).

EXAMPLE 2

Synthesis of compound (2) through methylation of compound (1)

Compound (2) was synthesized by methylating the hydroxyl group of compound (1) by a diazomethane method. The product was identified as follows.

1H-NMR: $\delta 3.85$ ($OCH_3$)
13C-NMR: $\delta 59.99$ ($OCH_3$), 60.22 ($OCH_3$), 171.81 (C=O), 156.90 (2-C), 144.60 (3-C), 144.44 (5-C), 160.48 (6-C), 14.62 (7-C), 31.21, 28.31, 26.72, 22.20, 13.77 (1'-C to 5'-C)

EXAMPLE 3

Synthesis of compound (3) through pyranthione derivation of compound (1)

A pyranthione derivative of compound (1) was synthesized by the method of F. Arndt et al. described in Chem. Ber., 57, 1903 (1924). More particularly, a solution of about 200 mg of compound (1) in 20 ml of benzene was combined with 430 mg of phosphorus pentasulfide and heated under reflux at about 85° C. for about 40 minutes. At the end of reflux, the reaction solution was filtered while it was hot. The filtrate was allowed to stand overnight at room temperature and then stripped of the benzene.

The residue was introduced into a silica gel column and developed with a hexane-ethyl acetate (3:1) mixture, isolating compound (3) which was identified as follows.

1H-NMR: $\delta 3.93$ ($OCH_3$)
13C-NMR: $\delta 179.79$ (C=S), 153.95 (6-C), 151.25 (2-C), 149.32 (5-C), 146.96 (3-C), 15.24 (7-C), 31.30, 28.97, 26.37, 22.27, 13.86 (1'-C to 5'-C)

EXAMPLE 4

Synthesis of compound (4) through pyridone derivation of compound (1)

A pyridone derivative of compound (1) was synthesized according to the method of M. A. F. Elkaschef et al. described in J. Chem. Soc., 4643 (1963). More particularly, a hydrolysis tube was charged with about 66 mg of compound (1) and 2 ml of 28% aqueous ammonia, sealed with a plug, and heated at about 110° C. for about 60 hours. At the end of reaction, the solvent was distilled off. The residue was purified through a silica gel column chromatograph by developing with a chloroform-methanol (20:1) mixture. The fraction was stripped of the solvent and recrystallized from methanol, obtaining compound (4) which was identified as follows.

13C-NMR: $\delta$163.33 (C=O), 130.41 (2-C), 135.41 (6-C), 143.28* (3-C), 141.88* (5-C), 13.97 (7-C), 30.97, 27.68, 27.26, 21.92, 13.50 (1'-C to 5''-C)
* exchangeable

EXAMPLE 5

Synthesis of compound (5) through otherwise derivation of compound (1)

Other derivatives can be synthesized from compound (1) by a proper combination of the reactions described in Examples 2 to 4, or according to any of the reactions described in Examples 2 to 4 by changing the reactant.

A methylpyridone derivative or compound (5) was synthesized according to the method of Example 4 by replacing the aqueous ammonia by methylamine. A pyridinethione derivative or compound (6) was synthesized according to the method of Example 4 by adding aqueous ammonia to compound (3). A methylpyridinethione derivative or compound (7) was synthesized according to the method of Example 4 by replacing the aqueous ammonia by methylamine. The resulting reaction products were purified by recrystallization. These products were identified to be compounds (5), (6), and (7) by mass spectra showing $M^+$: 239, $M^+$: 241, and $M^+$: 255, respectively.

EXAMPLE 6

Derivation of compound (1) in an Allium genus plant

Garlic bulbs were stripped of epidermis, fully washed with water, and subjected to the following three types of sterilization:

a) immersion in 0.1% aqueous solution of benzalkonium chloride for 5 minutes, b) immersion in 70% ethanol for 5 minutes, and c) immersion in 10% formalin for 10 minutes.

At the end of sterilization, the bulbs were fully washed with autoclave treated water and the root was cut off. The garlic was placed on lightly wet filter paper on a glass dish. The garlic at the top was covered with cotton wadding having a surface area of about 5 mm by 5 mm, which was impregnated with 20 $\mu$l of 1% aqueous solution of mercuric chloride. The glass dish was covered with a glass lid, sealed with film against air passage, and allowed to stand in the dark at room temperature for about 15 days. The amount of compound (1) produced was determined by high performance liquid chromatography (HPLC) during the process.

Similarly, those garlic samples which were chemically treated with $H_2O_2$, physically treated by partially scorching the plant, and treated with enzymes such as cellulase and pectinase were observed for the amount of compound (1) produced.

TABLE 1

| Sample | Amount of compound (1) produced ($\mu$g/g of wet weight) |
| --- | --- |
| Control | — |
| 1% $HgCl_2$ | 19 |
| 30% $H_2O_2$ | 79 |
| Cellulase | 14 |
| Pectinase | 130 |
| Scorch | 55 |

It was found that all the stressed garlic samples produced compound (1), but the non-stressed garlic sample (control) did not produce compound (1). It is thus evident that compound (1) is a stress compound of garlic.

It is to be noted that compound (1) was quantitatively determined by homogenizing a garlic sample (5 to 15 grams) along with about 30 to 40 ml of methanol and charging a 50 ml centrifugal sedimentation tube with the dispersion. The tube contents were made up to 50 ml, shaken for 10 minutes for extraction, and then subjected to centrifugal sedimentation at about 3,000 rpm for 10 minutes. The supernatant was a test liquid on which quantitative determination was carried out by HPLC under the following conditions.

Test liquid: 1 to 20 $\mu$l (injection)
Column: TSK gel ODS 80TM
Solvent: 0.05 M phosphoric acid buffer (pH 3.0) methanol (28:72)
Detection: UV 280 nm
Flow rate: 1.0 ml/min.

Figure 2:
FIG. 2 is a diagram showing the elution pattern by HPLC of an extract liquid of a mercuric chloride-treated garlic sample.

FIG. 1 is an elution pattern by HPLC of an extract liquid of the non-treated garlic sample, and FIG. 2 is an elution pattern by HPLC of an extract liquid of the garlic sample treated with mercuric chloride. For the stressed garlic sample, compound (1) eluted after 5 minutes 50 seconds as seen from FIG. 2. It is to be noted that the calibration line was prepared by the absolute calibration method using a methanol solution of compound (1).

EXAMPLE 7

Anti-carcinogenesis-promoter action

A sample (50 $\mu$g/ml) was added to HeLa cells on the second day of cultivation. After 24 hours, TPA ($5 \times 10^{-8}$ M) and $^{32}$Pi (50 $\mu$ci/culture) were added at the same time. After 4 hours, a phospholipid fraction was extracted to determine the radioactivity of $^{32}$Pi taken in the fraction.

The results are shown in Table 2.

TABLE 2

| Compound | Inhibition (%) of cell phospholipid synthesis promotion by TPA |
| --- | --- |
| (1) | 83.0 |
| (2) | 65.3 |
| (3) | 75.0 |
| (4) | 51.2 |
| (5) | 24.9 |
| (6) | — |
| (7) | 70.6 |
| (8) | 3.1 |
| (9) | 0 |
| (10) | 59.3 |
| (11) | 72.2 |
| (12) | 90.0 |
| (13) | 1.6 |

Compound (1) and some derivatives thereof were highly effective in inhibiting the phospholipid synthesis promotion by the carcinogenesis promoter or TPA.

The foregoing in vitro results suggest that compound (1) and derivatives thereof will also be effective in anti-carcinogenesis-promotion in vivo.

EXAMPLE 8

Inhibition of carcinogenesis

A compound was examined whether it could inhibit the promotion stage of mouse skin in vivo two-stage carcinogenesis. More particularly, a group of 15 ICR female mice was tested by once applying 100 μg of DMBA as an initiator to the skin of each mouse for initiation of carcinogenesis and then applying a test solution (identified below) twice a week. Inhibition of carcinogenesis was examined during the test which continued for 18 weeks in total. The promoter used was TPA.

Figure 3:
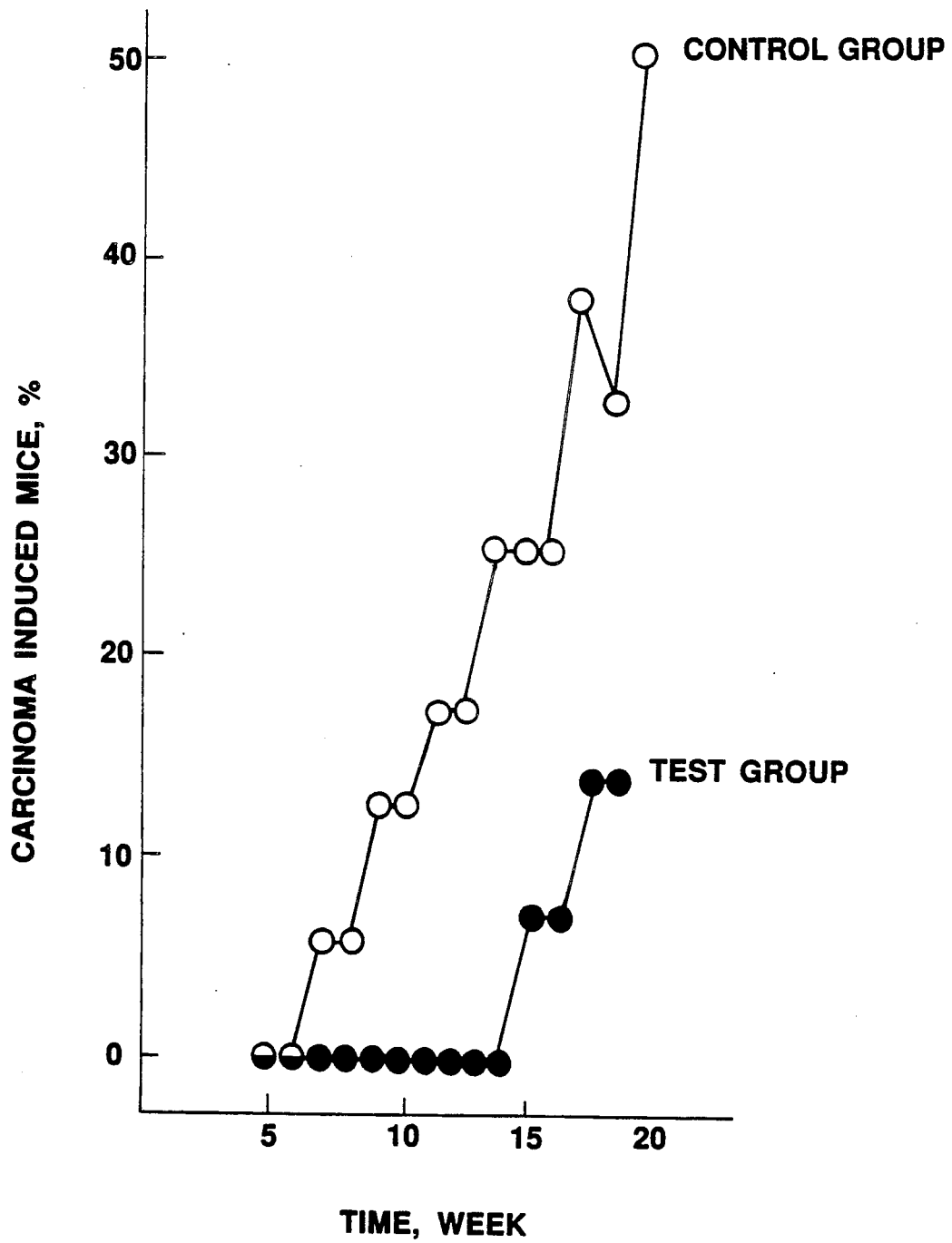
FIG. 3 is a diagram in which the percentage of carcinoma-induced mice is plotted relative to time, showing how compound (1) inhibits the promotion stage of mouse skin two-stage carcinogenesis.
Figure 4:
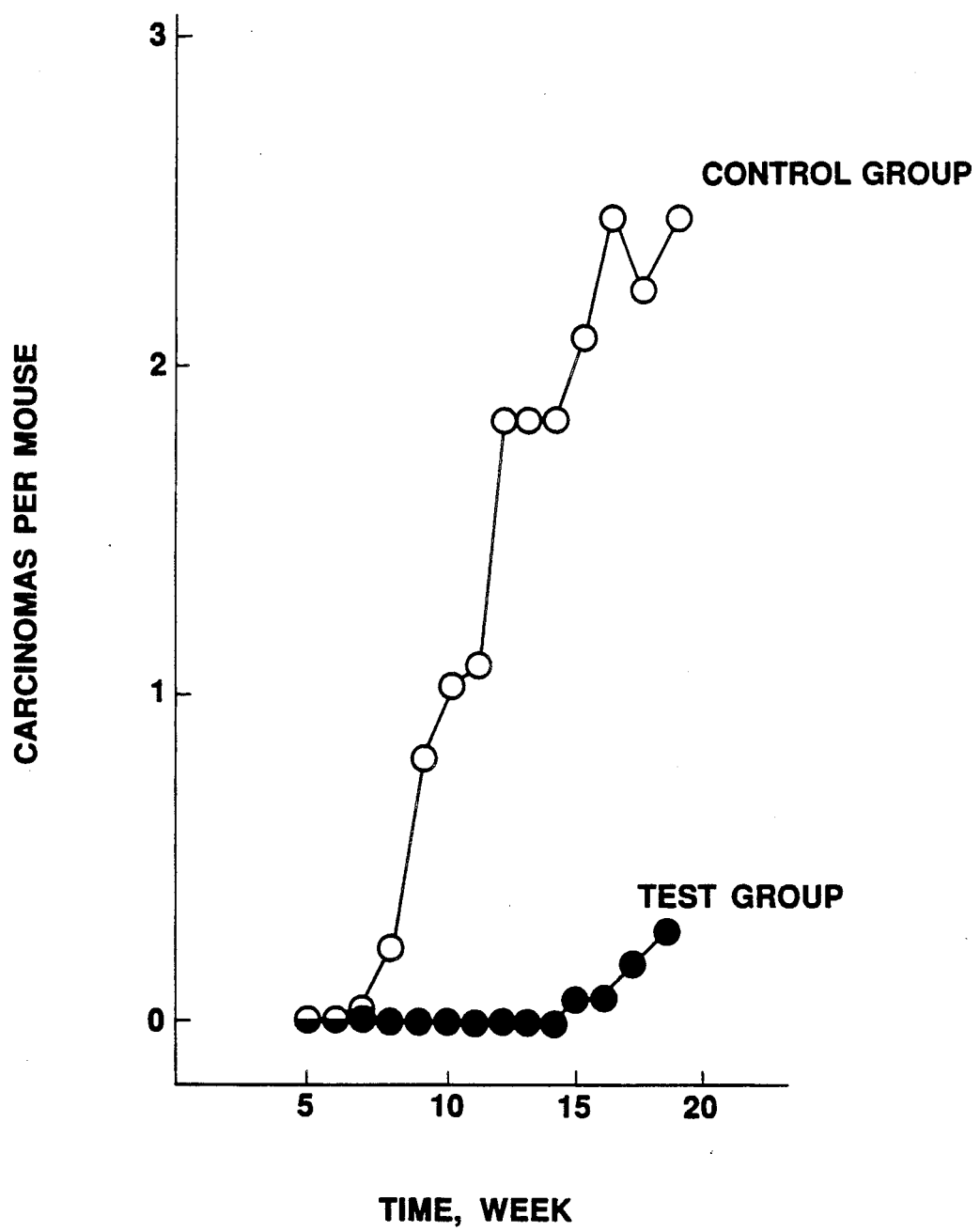
FIG. 4 is a diagram in which the number of carcinomas per mouse is plotted relative to time, also showing how compound (1) inhibits the promotion stage of mouse skin two-stage carcinogenesis.

Test group
1 μg of TPA applied
1 mg of compound (1) applied
Control group
1 μg of TPA applied The results are shown in FIGS. 3 and 4. FIG. 3 shows the percentage of cancer-induced mice versus time (in week). FIG. 4 shows the number of carcinomas per mouse versus time (in week).

In the control group to which compound (1) was not applied, carcinomas developed in 50% of mice at the 18th week from the beginning of carcinogenesis promotion, with the average number of carcinomas per mouse being 2.38.

In the test group to which compound (1) was applied, carcinomas developed in 13% of mice at the 18th week from the beginning of carcinogenesis promotion, with the average number of carcinomas per mouse being 0.22. It is thus evident that compound (1) is fully effective in inhibiting carcinogenesis.

EXAMPLE 9

Anti-carcinoma action

A. Inhibition against gastric carcinoma cells with time

Figure 5:
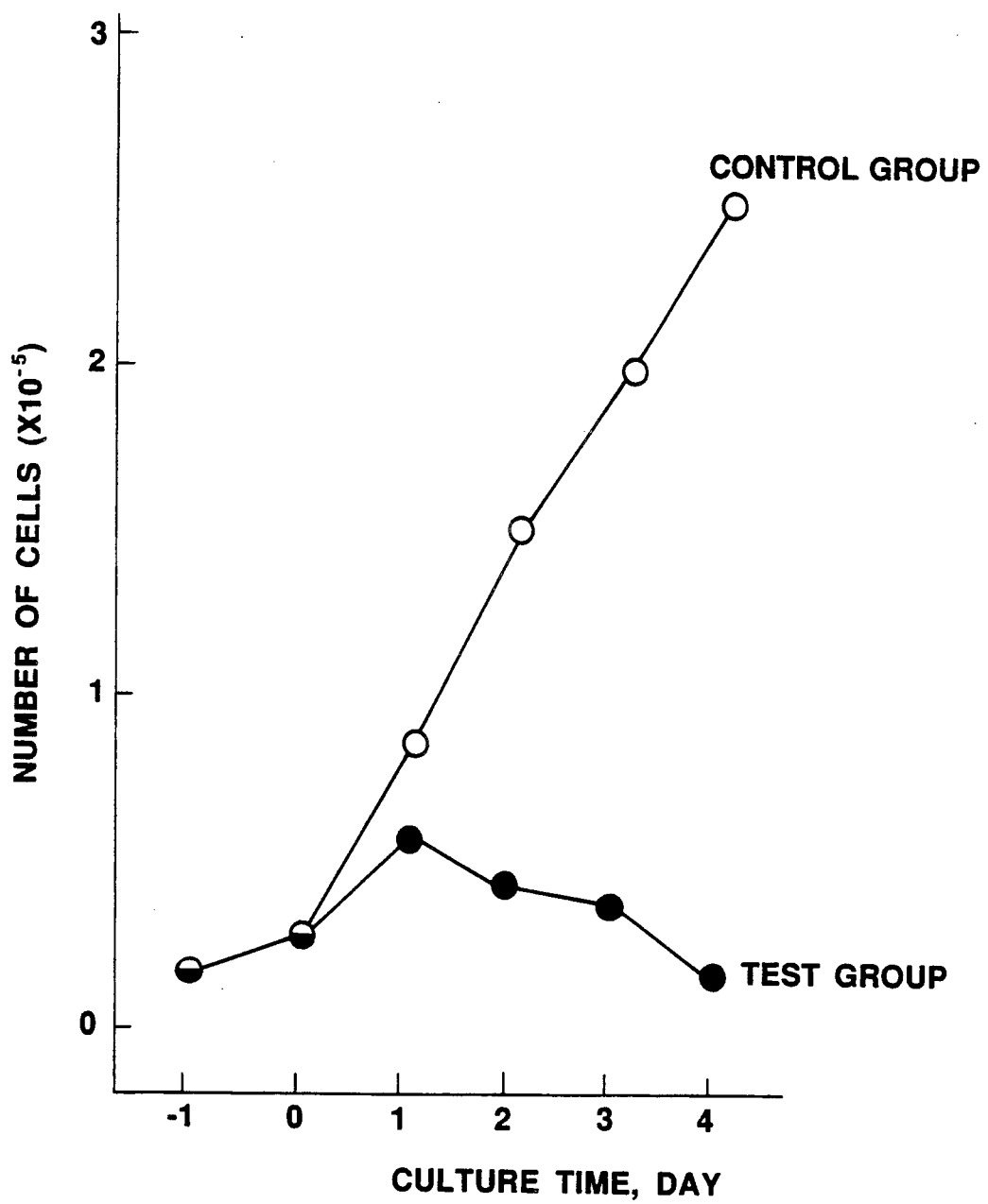
FIG. 5 is a diagram in which the number of cells is plotted relative to culture time, showing the carcinostatic effect of compound (1) against gastric carcinoma cells.

In a dish having a diameter of 3.5 cm, about $2 \times 10^4$ gastric carcinoma cells HGC-27 were spread and cultured. After one day, compound (1) was added to the culture in a concentration of 25 μg/ml and the number of cells was counted with the lapse of time. The results are shown in FIG. 5 in which the number of cells is plotted relative to the culturing time. It is evident that compound (1) is fully effective in inhibiting the propagation of gastric carcinoma cells HGC-27.

B. Inhibition against gastric carcinoma cells in varying concentrations

Figure 6:
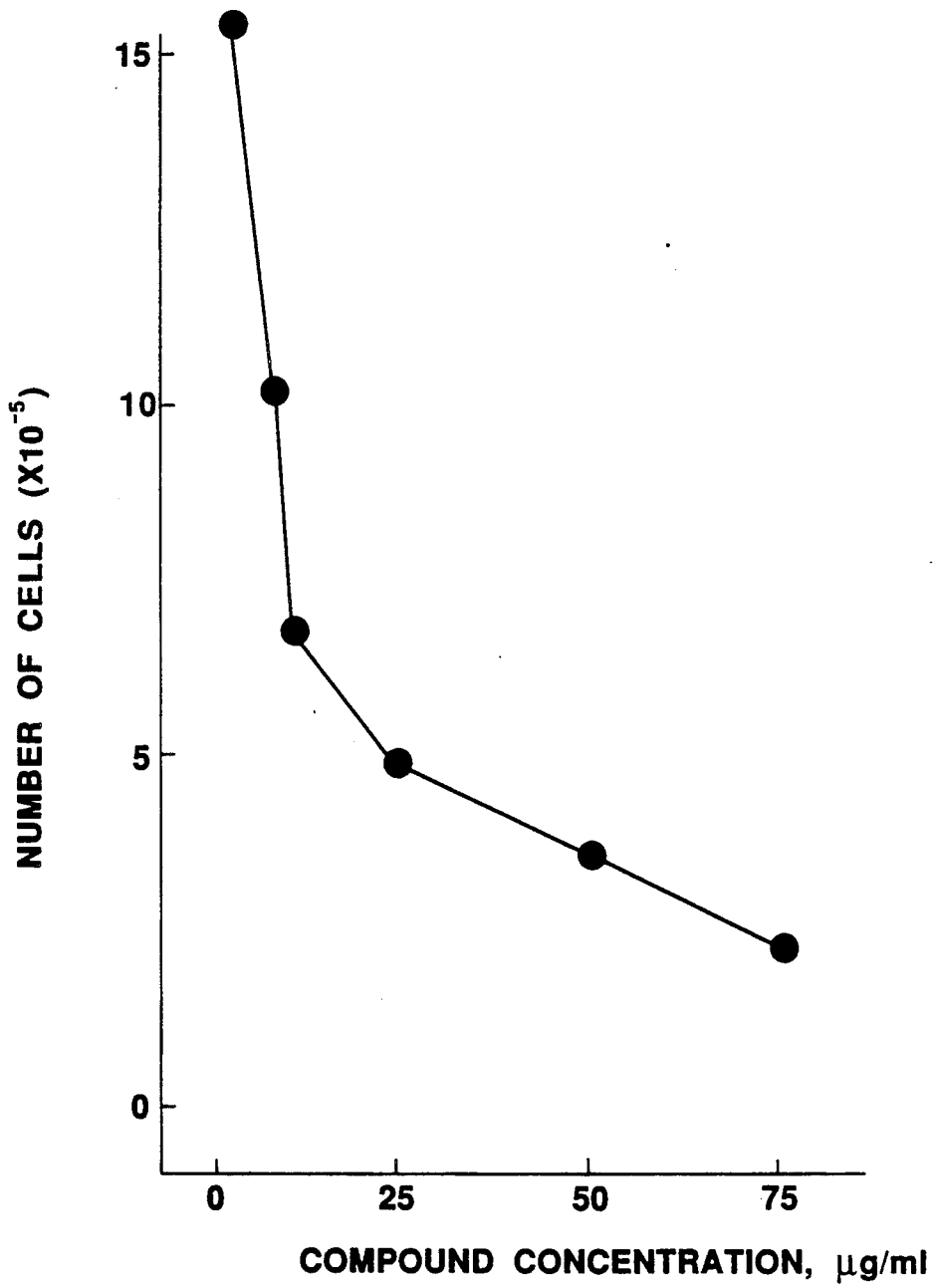
FIG. 6 is a diagram showing the dose dependency of the carcinostatic effect of compound (1) against gastric carcinoma cells.

In a dish having a diameter of 3.5 cm, about $2 \times 10^5$ gastric carcinoma cells HGC-27 were spread and cultured. After one day, compound (1) was added to the culture in varying concentrations of 5, 10, 25, 50, and 75 μg/ml. The number of cells was counted after two days. The results are shown in FIG. 6 in which the number of cells is plotted relative to the concentration of compound (1). It is evident that the inhibitory effect of compound (1) on gastric carcinoma cells HGC-27 is dependent on its concentration or dose, but it has a significant effect at a concentration as low as 5 μg/ml.

C. Inhibition against other carcinoma cells

Tested were three types of human carcinoma cells, pancreatic carcinoma cells PANC-1, cervical carcinoma cells HeLa, and neuroblastoma cells GOTO. For each type, about $2 \times 10^5$ cells were spread and cultured in a dish having a diameter of 3.5 cm. After one day, compound (1) was added to the culture in a concentration of 50 μg/ml. The number of cells was counted after two days. The results are shown in Table 3.

TABLE 3

| Cell | Number of cells ($\times 10^5$) | | |
|---|---|---|---|
| | Control | Test group | Test group/Control |
| PANC-1 | 8.95 | 2.45 | 27.3% |
| HeLa | 11.20 | 4.70 | 42.0% |
| GOTO | 10.95 | 4.85 | 44.3% |

It is evident that compound (1) has a strong propagation inhibiting effect not only on gastric carcinoma cells, but also on various other carcinoma cells.

The following examples illustrate the preparation of pharmaceutical compositions.

| Example 10: Powder | |
|---|---|
| Compound (1) | 500 mg |
| Lactose | 700 mg |
| Corn starch | 300 mg |
| Total | 1500 mg |

A powder was prepared by weighing 300 grams of compound (1), 420 grams of lactose, and 180 of corn starch, and mixing them for 10 minutes in a V-model mixer at 20 r.p.m.

| Example 11: Fine granules | |
|---|---|
| Compound (1) | 500 mg |
| Lactose | 625 mg |
| Corn starch | 300 mg |
| Hydroxypropyl cellulose | 60 mg |
| Magnesium stearate | 15 mg |
| Total | 1500 mg |

Fine granules were prepared by weighing 500 grams of compound (1), 625 grams of lactose, and 300 grams of corn starch, and charging a fluidized bed granulator (manufactured by Gratt Co.) with them. A binder solution was prepared by dissolving 60 grams of hydroxypropyl cellulose binder in 540 grams of pure water in a beaker. Fine granules were formed in the fluidized bed by spraying the binder solution. 1485 grams of the fine granules and 15 grams of magnesium stearate were mixed in a V-model mixer.

| Example 12: Granules | |
|---|---|
| Compound (1) | 500 mg |
| Lactose | 460 mg |
| Microcrystalline cellulose | 300 mg |
| Carboxymethyl-cellulose calcium | 150 mg |
| Hydroxypropyl cellulose | 90 mg |
| Total | 1500 mg |

Granules were prepared by weighing 1000 grams of compound (1), 920 grams of lactose, 600 grams of microcrystalline cellulose, 300 grams of carboxymethyl cellulose calcium, and 180 grams of hydroxypropyl cellulose, and mixing them for 15 minutes in a kneader at 30 r.p.m. Then 900 grams of pure water was added to the kneader and the contents were kneaded for a further 10 minutes at 30 r.p.m. The mixture was extrusion granulated through an extrusion granulator having a screen of 1.0 mm size. The granules were rectified and then dried for 16 hours in a hot air circulating tray dryer at 70° C. The dry granules were sieved to obtain a −12/+30 mesh fraction.

| Example 13: Dry syrup | |
|---|---|
| Compound (1) | 100 mg |
| Sodium citrate | 2.4 mg |
| Anhydrous citric acid | 2.2 mg |
| Powdered tragacanth | 2.7 mg |
| Sucrose | 881.7 mg |
| Hydroxypropyl cellulose | 10 mg |
| Perfume | 1 mg |
| Total | 1000 mg |

A dry syrup was prepared by weighing 100 grams of compound (1), 2.4 grams of sodium citrate, 2.2 grams of anhydrous citric acid, 2.7 grams of powdered tragacanth, and 881.7 grams of sucrose and mixing them in a V-model mixer. The mixture was pulverized by an atomizer and then granulated in a fluidized bed granulator using a 10% aqueous solution of hydroxypropyl cellulose binder. The granules were mixed with a perfume in a V-model mixer.

| Example 14: Hard capsules | |
|---|---|
| Compound (1) | 100 mg |
| Lactose | 142 mg |
| Microcrystalline cellulose | 95 mg |
| Maonesium stearate | 3 mg |
| Total | 340 mg |

Hard capsules were prepared by mixing 1000 grams of compound (1), 1420 grams of lactose, 950 grams of microcrystalline cellulose, and 30 grams of magnesium stearate, and filling No. 1 capsules with the mixture (340 mg per capsule) by means of a capsule filling machine (manufactured by Zanasi Co.).

| Example 15: Soft capsules | |
|---|---|
| Compound (1) | 100 mg |
| Medium chain fatty acid triglyceride | 235 mg |
| Aerogel 300 | 15 mg |
| Total | 350 mg |

Compound (1), 2000 grams, was pulverized by an atomizer so as to pass a 200 mesh screen. A vacuum emulsifying apparatus was charged with 4700 grams of medium chain fatty acid triglyceride, and the pulverized compound (1) and 300 grams of Aerosil 300 were added thereto. The contents were dispersed in vacuum to form a filling liquid. Soft capsules of a conventional composition were filled with the liquid, obtaining soft capsules.

| Example 16: Tablets | |
|---|---|
| Compound (1) | 100 mg |
| Lactose | 95 mg |
| Microcrystalline cellulose | 60 mg |
| Carboxymethyl cellulose calcium | 30 mg |
| Hydroxypropyl cellulose | 12 mg |
| Magnesium stearate | 3 mg |
| Total | 300 mg |

Granules were prepared from a mixture of 300 grams of compound (1), 285 grams of lactose, 180 grams of microcrystalline cellulose, and 90 grams of carboxymethyl cellulose calcium in a fluidized bed granulator using a 10% aqueous solution of hydroxypropyl cellulose. The granulated mixture was mixed with 9 grams of magnesium stearate in a V-model mixer and molded into tablets each weighing 300 mg in a tabletting machine.

| Example 17: Enteric coated tablets | |
|---|---|
| Coating composition | |
| Eudragit L30D-55* (30% solids) | 410 g |
| Macrogol 6000** | 14 g |
| Talc | 27 g |
| Pure water | 549 g |
| Total | 1000 g |

*Eudragit is the tradename of a methacrylic acid-ethyl acrylate copolymer commercially available from Rohn Pharma GmbH.
**Macrogol is the tradename of polyethylene glycol.

Using a HI-coater, the coating composition was spray coated on the tablets prepared in Example 16, obtaining enteric coated tablets each weighing 320 mg.

| Example 18: Sustained release tablets | |
|---|---|
| Compound (1) | 100 mg |
| Lactose | 92 mg |
| Microcrystalline cellulose | 60 mg |
| Eudragit NE30D (solids) | 45 mg |
| Magnesium stearate | 3 mg |
| Total | 300 mg |

Sustained release tablets were prepared by charging a fluidized bed granulator with 300 grams of compound (1), 276 grams of lactose, and 180 grams of microcrystalline cellulose. The mixture was granulated while spraying 450 grams of Eudragit NE30D (135 grams solids). The granules were mixed with 9 grams of magnesium stearate in a V-model mixer and then molded into tablets by means of a tabletting machine under a pressure of 1.5 tons. The tablets had a weight of 300 mg, a diameter of 9 mm, and a hardness of 15 kg.

The tablets were tested for dissolution.

The test method was Method 2 (rotating paddle method) of the dissolution test prescribed in the Japan Pharmacopoeia, 11th Edition. The tablets were placed in a test solution which was paddled at 37° C. and 100 rpm. The amount of compound (1) dissolved out was determined at intervals. The first fluid was used for 0 to 2 hours and the second fluid was used after 2 hours. The results are shown in Table 4.

TABLE 4

| | Dissolution test | | | | | | | |
|---|---|---|---|---|---|---|---|---|
| Time (hour) | ½ | 1 | 2 | 3 | 4 | 6 | 8 | 10 |
| Amount (%) | 7.1 | 16.5 | 35.4 | 50.2 | 59.7 | 71.3 | 82.3 | 90.4 |

Figure 7:
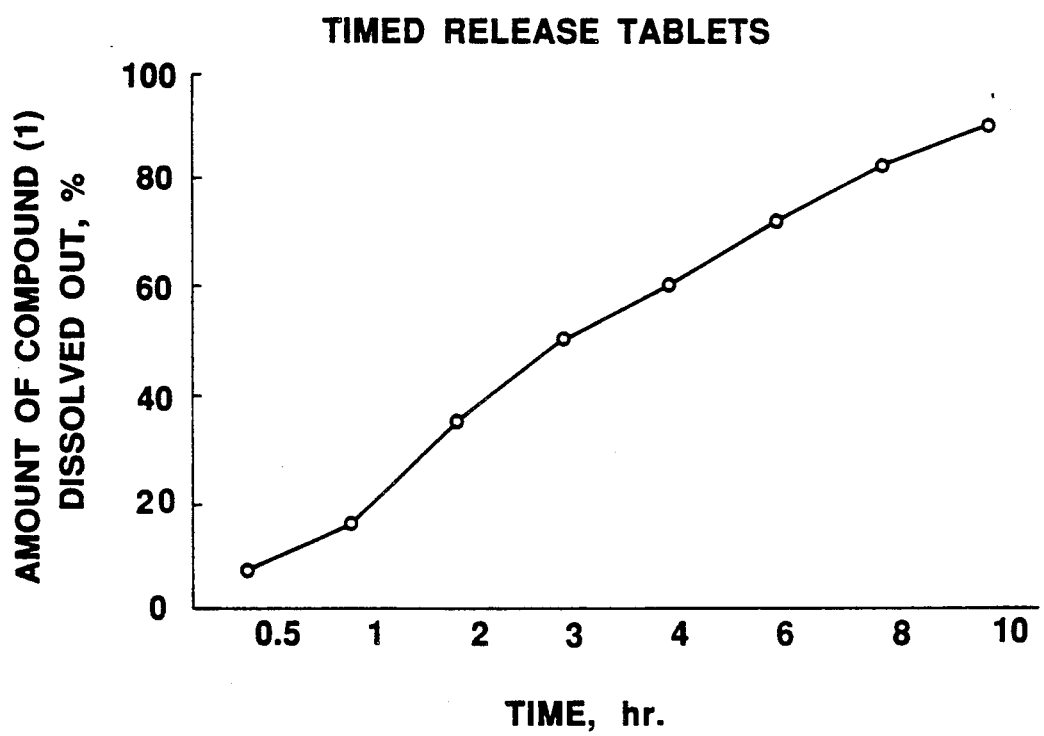
FIG. 7 is a diagram showing the percentage of compound (1) dissolved out of timed release tablets in a dissolution test.

The results are also shown in the graph of FIG. 7 in which the percentage of compound (1) dissolved out is plotted as a function of time (in hour).

It is evident from Table 4 and FIG. 7 that the tablets gradually release the active ingredient.

| Example 19: Oleaginous ointment | |
|---|---|
| Compound (1) | 10% by weight |
| Liquid paraffin | 10% |
| White vaselin | 80% |

| Example 19: Oleaginous ointment | |
|---|---|
| Total | 100% |

Compound (1), 200 grams, was pulverized by an atomizer so as to pass a 200 mesh screen. A vacuum emulsifying apparatus was charged with 200 grams of liquid paraffin and 1600 grams of white vaseline, which were heated at 80° C. under vacuum with stirring to form a solution. Then the pulverized compound (1) was added to the solution and dispersed therein at 80° C. in vacuum. The dispersion was cooled down to room temperature and taken out.

| Example 20: Suspension lotion | |
|---|---|
| | % by weight |
| Compound (1) | 5 |
| Carboxymethyl cellulose sodium | 1 |
| Tween 80* | 0.5 |
| Benzalkonium chloride | 0.025 |
| Methyl para-hydoxybenzoate | 0.025 |
| Propyl para-hydoxybenzoate | 0.015 |
| Silicone antifoaming agent | 0.05 |
| 99% ethanol | 0.25 |
| Purified water | 93.135 |
| Total | 100.000% |

*nonionic surface active agent by Atlas Co.

Carboxymethyl cellulose sodium, 1 gram, was dissolved in 68 grams of purified water. Compound (1), 5 grams, was pulverized by an atomizer so as to pass a 200 mesh screen. Another solution was prepared by dissolving 0.025 grams of methyl para-hydoxybenzoate and 0.015 grams of propyl para-hydoxybenzoate in 0.25 grams of 99% ethanol. A vacuum emulsifying apparatus was loaded with the solutions, pulverized compound (1), 25.135 grams of purified water, 0.5 grams of Tween 80, 0.05 grams of silicone antifoaming agent, and 0.025 grams of benzalkonium chloride. The contents were dispersed at 80° C. in vacuum. The product was cooled down to room temperature and taken out.

| Example 21: Syrup | |
|---|---|
| Compound (1) | 250 mg |
| Sucrose | 1500 mg |
| D-sorbitol solution (70%) | 1250 mg |
| Methyl para-hydoxybenzoate | 1.5 mg |
| Propyl para-hydoxybenzoate | 0.75 mg |
| Sodium citrate | 50 mg |
| Citric acid | 7.5 mg |
| Perfume | 5 mg |
| Purified water | 1935.25 mg |
| Total | 5000.00 mg |

Compound (1), 125 grams, was pulverized by an atomizer so as to pass a 200 mesh screen. A vacuum emulsifying apparatus was loaded with 750 grams of sucrose, 625 grams of 70% D-sorbitol solution, 0.75 grams of methyl para-hydoxybenzoate, 0.375 grams of propyl para-hydoxybenzoate, 25 grams of sodium citrate, 3.75 grams of citric acid, and 967.625 grams of purified water. The contents were heated to 80° C. to form a solution. To the solution was added the pulverized compound (1). After the contents were dispersed, the dispersion was cooled down to room temperature. A perfume was added to and mixed with the dispersion, which was then taken out.

| Example 22: Suppository | |
|---|---|
| Compound (1) | 500 mg |
| Higher fatty acid triglyceride | 1500 mg |
| Total | 2000 mg |

Compound (1), 500 grams, was pulverized in an atomizer so as to pass a 200 mesh screen. Higher fatty acid triglyceride, 1500 grams, was melted by heating to 50° C. A vacuum emulsifying apparatus was loaded with the pulverized compound (1) and the melt. The contents were dispersed at 50° C. in vacuum. The dispersion was cooled to 37° C. and cast into mold cavities where it was slowly cooled.

| Example 23: Intramuscular suspended injection | |
|---|---|
| Compound (1) | 20 mg |
| Aluminum stearate | 2 mg |
| Soybean oil | totaling to 2 ml |

Compound (1), 100 grams, was pulverized and maintained in a sterile, dust-free condition. Also, 10 grams of aluminum stearate and 9890 ml of soybean oil were maintained in a sterile, dust-free condition. Of course, they were pyrogen-free. The three ingredients were mixed into a suspension in a clean room condition. Vials were filled with the suspension, closed with a rubber plug, and covered with an aluminum cap in an inert gas purged atmosphere.

| Example 24: Suspended eye-drop | |
|---|---|
| Compound (1) | 50 mg |
| Citric acid monohydrate | 29 mg |
| Dibasic sodium phosphate dihydrate | 140 mg |
| Sodium chloride | 13 mg |
| Benzalkonium chloride | 2 mg |
| Purified water | totaling to 10 ml |

Compound (1), 100 grams, was pulverized and maintained in a sterile, dust-free condition. In 19532 ml of pure water were dissolved 58 grams of citric acid monohydrate, 280 grams of dibasic sodium phosphate dihydrate, 26 grams of sodium chloride, and 4 grams of benzalkonium chloride. The solution was passed through a 0.22 μm membrane filter for sterilization. The pulverized compound (1) was blended with and dispersed in the filtrate in a clean room condition, obtaining a filling liquid. Then eye drop bottles which had been cleaned and sterilized along with nozzles and caps were filled with the liquid in a clean room.

Although some preferred embodiments have been described, many modifications and variations may be made thereto in the light of the above teachings. It is therefore to be understood that within the scope of the appended claims, the invention may be practiced otherwise than as specifically described.

We claim:

1. A heterocyclic compound of the general formula:

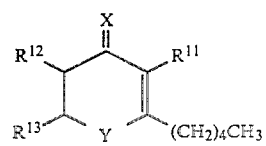

wherein $R^{11}$ is a hydroxyl group or a lower alkoxy group, $R^{12}$ is a lower alkoxy group, $R^{13}$ is a lower alkyl group, X is an oxygen atom or a sulfur atom, and Y is an oxygen atom, or a salt thereof.

2. A carcinostatic composition, comprising an effective amount of a heterocyclic compound or a salt thereof as set forth in claim 1 as an active ingredient and a pharmaceutically acceptable carrier, wherein said effective amount is from 10 mg to 10 grams.

3. The heterocyclic compound of claim 1, which is selected from the group consisting of 3-hydroxy-6-methyl-5-methoxy-2-pentyl-4H-pyran-4-one, 6-methyl-3,5-dimethoxy-2-pentyl-4H-pyran-4-one, and 3-hydroxy-6-methyl-5-methoxy-2-pentyl-4H-pyran-4-thione.

4. The heterocyclic compound of claim 1, wherein $R^{13}$ is a saturated linear alkyl group having 1 to 6 carbon atoms.

5. The heterocyclic compound of claim 4, wherein $R^{13}$ is a methyl group.

6. The carcinostatic composition of claim 2, wherein said heterocyclic compound is selected from the group consisting of 3-hydroxy-6-methyl-5-methoxy-2-pentyl-4H-pyran-4-one, 6-methyl-3,5-dimethoxy-2-pentyl-4H-pyran-4H-pyran-4-one, and 3-hydroxy-6-methyl-5methoxy-2-pentyl-4H-pyran-4-thione, hydroxy-6-methyl-5-methoxy-2-pentyl-4-pyridone, hydroxy-1,6-dimethyl-5-methoxy-2-pentyl-4-pyridone, and hydroxy-1,6-dimethyl-5-methoxy-2-pentyl-4-pyridinethione.

* * * * *

UNITED STATES PATENT AND TRADEMARK OFFICE
CERTIFICATE OF CORRECTION

PATENT NO. :   5,093,505
DATED      :   MARCH 3, 1992
INVENTOR(S):   HOYOKU NISHINO ET AL

It is certified that error appears in the above-identified patent and that said Letters Patent is hereby corrected as shown below:

In the Abstract; the formula

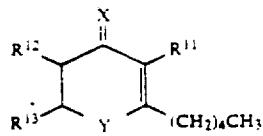

should read

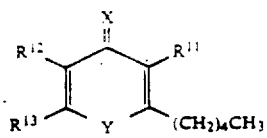

Column 16:

In Claim 1, line 1; the formula

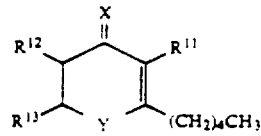

should read

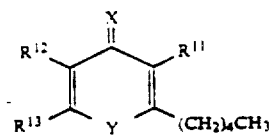

UNITED STATES PATENT AND TRADEMARK OFFICE
CERTIFICATE OF CORRECTION

PATENT NO. : 5,093,505

DATED : March 3, 1992

INVENTOR(S) : Hoyoku Nishino, et al.

It is certified that error appears in the above-identified patent and that said Letters Patent is hereby corrected as shown below:

should read

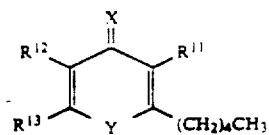

Signed and Sealed this

Sixth Day of July, 1993

Attest:

MICHAEL K. KIRK

Attesting Officer

Acting Commissioner of Patents and Trademarks